US00PP22807P3

(12) United States Plant Patent
Korlipara

(10) Patent No.: US PP22,807 P3
(45) Date of Patent: Jun. 19, 2012

(54) ***ECHINACEA* PLANT NAMED 'HOT LAVA'**

(50) Latin Name: ***Echinacea* hybrid**
Varietal Denomination: Hot Lava

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 295 days.

(21) Appl. No.: 12/798,836

(22) Filed: Apr. 12, 2010

(65) Prior Publication Data

US 2011/0252530 P1 Oct. 13, 2011

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP16,424 P2 * 4/2006 Saul ..... Plt./428
PP18,839 P2 * 5/2008 Korlipara ..... Plt./428
PP19,427 P2 * 11/2008 Korlipara ..... Plt./428

OTHER PUBLICATIONS

Anonymous. *Echinacea* 'Hot Lava' PPAF (Perennial Coneflower) available at: http://www.plantdelights.com/Echinacea-Hot-Lava_PPAF-Perennial-Coneflower/productin accessed Jul. 12, 2011.*
UPOV ROM GTITM Computer Database, GTI Jouve Retrieval Software 2011/03 Citation for 'Hot Lava'.*

* cited by examiner

*Primary Examiner* — Wendy C Haas
(74) *Attorney, Agent, or Firm* — Klarquist Sparkman, LLP

(57) ABSTRACT

A new and distinct *Echinacea* plant named 'Hot Lava' characterized by large, orange red inflorescences with prominent dark cones, well-branched upright flower stalks, and excellent vigor.

1 Drawing Sheet

Botanical denomination: *Echinacea* hybrid.
Variety designation: 'Hot Lava'.

The present invention relates to a new and distinct cultivar of *Echinacea* and given the cultivar name 'Hot Lava'. *Echinacea* is in the family Asteraceae. This new cultivar originated as a fourth generation seedling from a planned breeding program using the parents *Echinacea paradoxa* and *Echinacea purpurea* 'Ruby Giant' (unpatented) for the initial cross. The exact parents of this selection are unknown, unnamed proprietary, unreleased plants.

This new *Echinacea* cultivar is distinguished by:

1. Large, orange red inflorescences with prominent dark cones
2. Well-branched upright flower stalks
3. Excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the flowers of *Echinacea* 'Hot Lava' on a plant growing in the ground in full sun in the field in late summer in Canby, Oreg.

FIG. 2 shows a habit shot of a one-year-old plant in the summer in the trial bed in Canby, Oreg.

DETAILED PLANT DESCRIPTION

The following is a detailed description of the new *Echinacea* cultivar based on observations of 18-month old specimens growing in the ground in the field in full sun in the trial bed under typical outdoor conditions in Canby, Oreg. The plants had been moved from one trial field to another the fall before. Canby is in Zone 8 on the USDA Hardiness map Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, fifth edition.

Plant:

*Type.*—Herbaceous perennial.
*Hardiness.*—USDA Zones 4 to 9.
*Size.*—Grows to 68 cm wide and 82 cm tall to top of flowers.
*Form.*—Basal clump.
*Vigor.*—Excellent.
*Roots.*—Roots develop easily from cuttings from the crown.

Stem (flowering):

*Type.*—Ascending.
*Size.*—Branching up to 6 times to 55 cm tall (to the upper most leaves) and 7 mm wide at base.
*Number of stems from the crown.*—12.
*Internode length.*—4 to 12 cm.
*Surface texture.*—Strigose.
*Color.*—Yellow Green 146B mottled with Yellow Green 145C.

Leaf (basal):

*Type.*—Simple.

*Shape.*—Lanceolate.

*Arrangement.*—Basal.

*Blade size.*—Grows to 14 cm long and 5 cm wide.

*Margins.*—Entire.

*Apex.*—Acute.

*Base.*—Attenuate.

*Surface texture.*—Strigose on both sides.

*Venation.*—Pinnate.

*Color.*—Topside, Green 137A with the vein Green 138C and bottom side closest to Yellow Green 137B with the vein Green 138C.

*Petiole description.*—Grows to 13 cm long and 4 mm wide, glabrous, Yellow Green 146C.

Leaf (stem):

*Type.*—Simple.

*Shape.*—Ovate to lanceolate.

*Arrangement.*—Alternate.

*Blade size.*—Grows to 9.5 cm long and 4.5 cm wide.

*Margins.*—Coarsely serrate.

*Apex.*—Acute to acuminate.

*Base.*—Attenuate, continuing down petiole, clasping.

*Surface texture.*—Strigose on both sides.

*Venation.*—Pinnate.

*Color.*—Topside, Yellow Green 147A with the vein Yellow Green 147B and bottom side closest to Yellow Green 147B with the vein Yellow Green 145B.

*Petiole description.*—Grows to 1 cm long and 4 mm wide, strigose, Yellow Green 145B on back and top side Yellow Green 146B tinted Greyed Orange 166A.

Inflorescence:

*Type.*—Composite on terminal stalked heads.

*Number of flowering stems per plant in summer.*—12 from the crown, some branching.

*Flowering stem.*—Grows to 80 cm tall from the base of the plant to the terminal flower and can grow to 27 cm long from the top leaf to the base of a flower head; branched, 1 to 6 inflorescences per stem; diameter growing to 5 mm wide near the flower head; strigose, Yellow Green 146B mottled with Yellow Green 145C.

*Size.*—Grows to 12 cm wide and 4.5 cm deep as disc enlarges.

*Form.*—Ray florets held mostly perpendicular to the stem, some dropping down slightly; mature disc is conic.

*Immature inflorescence.*—3.5 cm wide and 2.2 cm deep, ray florets held at a 45 degree angle and rolled up so only the back color shows, Red Purple 64A.

*Ray florets.*—Without pistil or stamen, 20 to 25 in number, oblanceolate with the tip cupped and 2 to 3 toothed (each acute), entire margins, base attenuate, grows to 5 cm long and 11 mm wide, glabrous on both sides; sometimes with upward projections from base, to 18 mm long and 2 mm wide; topside color when first fully open Greyed Orange 169A darkening to a bicolor of Greyed Orange 169A on the top to Red 45A near the cone, mature ray florets Greyed Orange 173B on top ⅔ and Greyed Purple 187D on bottom ⅓; bottom side Greyed Purple 186B to C.

*Disc.*—Slightly convex becoming conic, becoming 35 mm deep and 40 mm wide with maturity, color from outside in Greyed Purple 187B on old bracts and new bract tips, Yellow Orange 23B on younger bracts, and Yellow Green 147A as the base color.

*Disc florets.*—About 450 in number, with pistil and stamen, 10 mm long and 1.5 mm wide, each with one persistent, very stiff bract (12 mm long and Greyed Purple 187A on tip to Yellow Orange 23B, Yellow Green 146C on middle ⅓, White NN155B on bottom ⅓); corolla 6 mm long and 1.5 mm wide, 5 lobed, glabrous, Yellow Green 146D with Greyed Purple 187A on lobes, pistil 11 mm long, ovary 4 mm long, White NN155A, style 5 mm long, Greyed Purple 187A with an extruding, 2-branched stigma spreading 2.5 mm wide, Greyed Purple 187; stamen 4 in number, 6 mm long, anthers 2.5 mm long and Greyed Purple N186A, filaments 3.5 mm long, Yellow Green 145D, pollen Yellow Orange 14B.

*Phyllaries.*—In 4 leafy series, area 35 mm wide and 17 mm deep, lobes lanceolate in shape, reflexed, grow to 13 mm long and 3 mm wide, margins strigose, tip acute, Yellow Green 147A.

*Receptacle.*—Grows to 12 mm wide and 20 mm deep, White 155B.

*Bloom period.*—July through October in Canby, Oreg.

*Fragrance.*—Light, floral.

*Lastingness.*—Each inflorescence lasts about two weeks in Canby, Oreg.

Seeds: Average number of 10 seeds/head, each 5 mm long and 2.5 mm wide, oval, Greyed Green 197A.

*Fertility.*—Low.

Disease and pests: *Echinacea* are susceptible to leaf miners, powdery mildew, bacterial spots, and gray mold. None of these have been observed on plants grown under commercial conditions in Canby, Oreg. No resistance is known.

COMPARISONS TO SIMILAR *ECHINACEA*

Compared to *Echinacea* 'Tiki Torch' (U.S. Plant Pat. No. 18,839), the new cultivar has a flower that is redder.

Compared to *Echinacea* 'Tomato Soup' (U.S. Plant Pat. No. 19,427), the new cultivar has more orange in the flower and fades to a bicolor rather than being red and fading to a dull red.

Compared to *Echinacea* 'Sunset' (U.S. Plant Pat. No. 16,424), the new variety has larger flowers with deeper orange red color.

I claim:

1. A new and distinct *Echinacea* plant as herein illustrated and described.

* * * * *

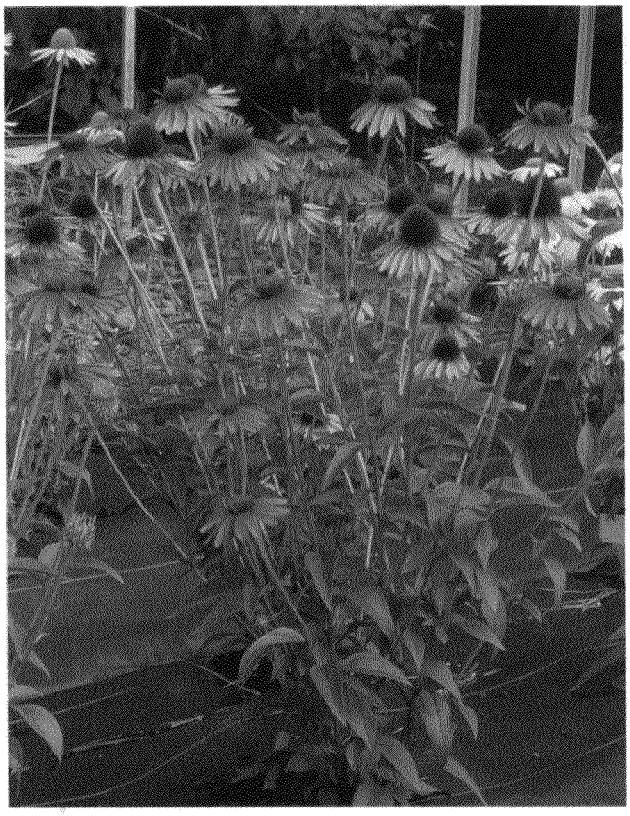

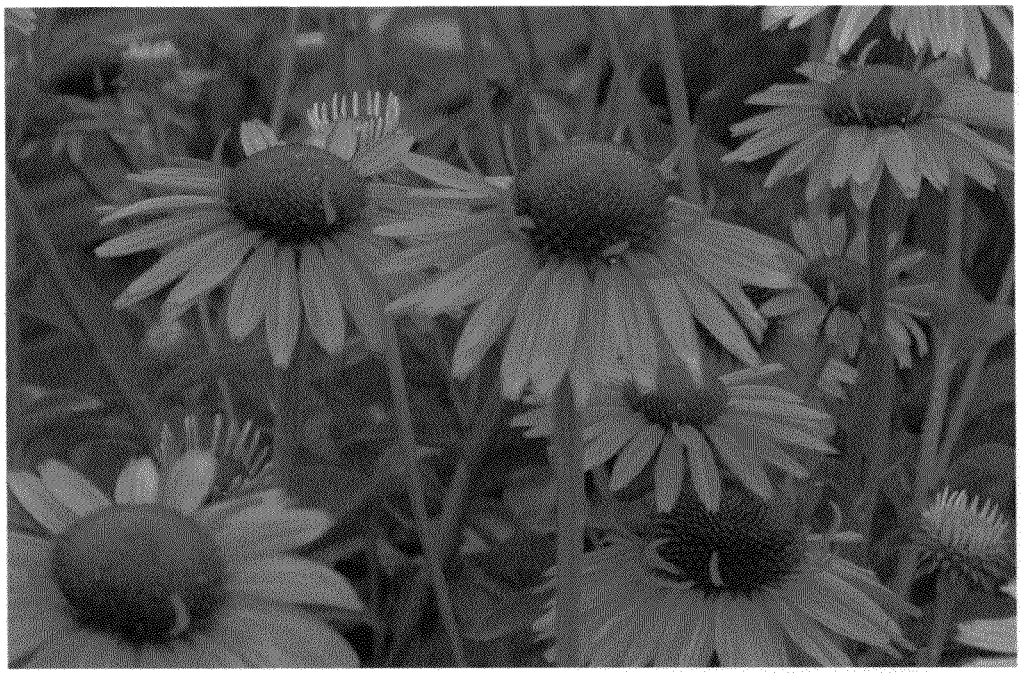
Figure 1 above, Figure 2 below